(12) United States Patent
Ranoux et al.

(10) Patent No.: US 7,282,363 B1
(45) Date of Patent: *Oct. 16, 2007

(54) INTRAVAGINAL CULTURE (IVC) METHOD AND CONTAINER THEREFOR

(75) Inventors: Claude Ranoux, Winchester, MA (US); Francis G. Gleason, Jr., Ashland, MA (US)

(73) Assignee: Bio X Cell, Inc., Winchester, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/240,935

(22) PCT Filed: Apr. 18, 2000

(86) PCT No.: PCT/EP00/04176

§ 371 (c)(1),
(2), (4) Date: Apr. 10, 2003

(87) PCT Pub. No.: WO01/78611

PCT Pub. Date: Oct. 25, 2001

Related U.S. Application Data

(63) Continuation of application No. 08/854,272, filed on May 9, 1997, now Pat. No. 6,050,935.

(51) Int. Cl.
*C12M 1/24* (2006.01)
*C12M 3/00* (2006.01)
(52) U.S. Cl. .................. 435/304.1; 435/288.1; 435/307.1; 600/33; 600/34; 600/35; 604/906
(58) Field of Classification Search .............. 600/33, 600/34, 35; 435/304.1, 288.1, 307.1; 604/906
See application file for complete search history.

(56) References Cited

U.S. PATENT DOCUMENTS

| 2,142,278 | A | | 1/1939 | Mendelson |
| 3,814,522 | A | | 6/1974 | Clark et al. |
| 3,998,211 | A | * | 12/1976 | Bucalo ........................ 600/582 |
| 4,105,415 | A | | 8/1978 | Lovett |
| 4,902,286 | A | | 2/1990 | Ranoux |
| 5,030,421 | A | * | 7/1991 | Muller ........................ 422/102 |
| 5,297,599 | A | | 3/1994 | Bucheli |
| 5,681,742 | A | * | 10/1997 | MersKelly et al. ....... 435/288.1 |
| 5,691,194 | A | | 11/1997 | Gordon |
| 5,928,935 | A | * | 7/1999 | Reuss et al. ............. 435/288.1 |
| 6,050,935 | A | * | 4/2000 | Ranoux et al. .............. 600/33 |
| 2004/0157205 | A1 | * | 8/2004 | Etheredge et al. ........... 435/1.1 |

FOREIGN PATENT DOCUMENTS

EP 0 529 595 A1 3/1993

* cited by examiner

*Primary Examiner*—Gladys J P Corcoran
*Assistant Examiner*—Nathan A. Bowers
(74) *Attorney, Agent, or Firm*—Young & Thompson (57) ABSTRACT

A fertilization and culture container, e.g. for intravaginal use, comprises a container body having an orifice for introducing a culture medium, one or more oocytes and sperm, resealable closure means for selectively opening and closing the container body orifice, the container body having a main chamber for receiving the culture medium, oocytes and sperm and a microchamber for collecting for retrieval of one or more embryos. The container body has elements for restricting access of retrieval catheter or pipette relative to the microchamber. At least a portion of a sidewall of the container body defining said microchamber is transparent and of optical quality for microscopic inspection of embryos prior to and/or during retrieval with a catheter or a pipette.

26 Claims, 3 Drawing Sheets

INTRAVAGINAL CULTURE (IVC) METHOD AND CONTAINER THEREFOR

This invention relates to a container for fertilization and culture of mammalian, and in particular human, oocytes and an embryo transfer method employing such a container, in particular for intravaginal use.

Conventional in vitro fertilization (IVF) techniques are notoriously complex and have tended to become even more so since intracytoplasmic sperm injection (ICSI) was added to the panoply of assisted reproductive technologies.

Typically, IVF involves aerobic and sterile culturing of embryos in Petri dishes at 37° C. in a 5% $CO_2$ enriched atmosphere. It requires cumbersome and expensive equipment such as a $CO_2$ incubator controlled at 37° C. 24-hours a day, during the two or three days required for fertilization and culture.

IVF also involves the use of many pieces of disposable equipment and media for the numerous steps carried out over the 48 or 72 hours of treatment of gametes and embryos in the $CO_2$ enriched incubator. Many include delicate manipulations requiring considerable skill and dexterity of a laboratory biologist. One of these consists in denuding the embryo of cumulus cells prior to implantation.

One of the co-inventors, Claude Ranoux, developed a new procedure known as intravaginal culture (IVC) which comprises maturation of gametes, fertilization and embryo development in a sealed container filled with a suitable culture medium and placed in the vaginal cavity which serves as an incubator. This procedure and the fertilization and culture container are disclosed in U.S. Pat. No. 4,902,286 issued Feb. 20, 1990 and U.S. Pat. No. 5,135,865 issued Aug. 4, 1992.

Figure 2:
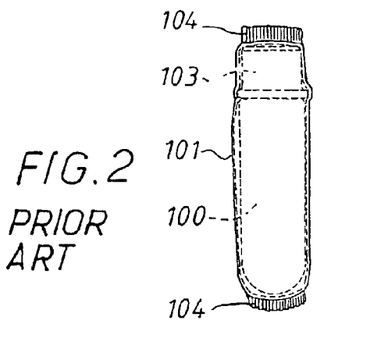
FIG. 2 is a side elevation view of a prior art Nunc cryotube and cryoflex envelope used to date for IVC.

All IVC procedures for experimental and clinical purposes have to date been performed using a polypropylene cryotube, designated by reference numeral 100 as shown in FIG. 2, manufactured by Nunc, of Kamptrup, Denmark and hermetically closed and sealed in a polyethylene cryoflex envelope 101 also manufactured by Nunc. The cryotubes and associated cryoflex envelopes were designed for cryopreservation of tissue specimens. The Nunc cryotube and cryoflex envelope have considerable drawbacks when used to perform IVC.

Among these drawbacks is the fact that the tube has to be filled virtually to the free edge or brim of the (externally threaded) tube neck to avoid the formation of air bubbles which could otherwise interfere with fertilization. Also in practice, sperm must be introduced into the tube before the oocytes because the turbulence produced during sperm injection into the culture medium might otherwise carry one or more oocytes to the surface of the medium and cause them to spill out over the brim. The cumulus of the oocytes have some occluded air bubbles which may cause them to float to the surface of the culture medium only to be lost when the cap 103 is screwed on to the neck of the tube.

Likewise, when the threaded cap is screwed on to the neck, there is a risk of culture medium overflow, entraining one or more oocytes out of the tube.

The cryoflex envelope 101 has to be sealed around the tube to protect the tube from contamination during vaginal residence. In practice, this requires heating a crimping tool or pliers and softening and crimping each of the ends of the tube to form serrated welds or seals 104. The free edges of the welds in turn must then be clipped and/or shaped with a cutter to eliminate corners, but this does not avoid all discomfort or even injury in the course of lodgment in the posterior fornix as the free transverse edges of the seals remain both rough and sharp. Also, a single size tube cannot be used for all individuals owing to anatomical incompatibility.

Many of these drawbacks of the Nunc cryotube are obviated by the container disclosed in Ranoux U.S. Pat. No. 4,902,286 and U.S. Pat. No. 5,135,865. The container body comprises a membrane or valve which prevents the loss of oocytes during their introduction or the introduction of sperm. Moreover, the membrane or valve limits the area of contact between the culture medium and the surroundings and tends to maintain the pH of the culture medium stable. These patents also disclose a flexible rubberized ring from which is appended a rubber pouch for accommodating the container. The diameter of the ring has to be determined individually, like a diaphragm, as a function of the size of the cervix. The tube is intended to be held in the posterior fornix of the vagina but may drop out and then held dangling from ring and out of contact with the vaginal walls.

The development of IVC has been hindered by the lack of a container the use of which is simple and safe, and which does not involve the high level of laboratory skill that have been required to date and which can avoid transfer of the embryos from the container to a Petri dish for microscopic inspection before their ultimate transfer to the uterine cavity.

To be sure, Ranoux U.S. Pat. No. 5,084,004 discloses an intra-uterine fertilization container with an exit area for access to the uterine cavity and transfer of one or more fertilized oocytes from the container to the cavity. Such a device is unsuitable for use in the vagina owing to the lack of sterile conditions liable to contaminate the embryos. Moreover, the preferred embodiments involve the use of a special holding device which is introduced into the cervix and a second section located in the vagina external to and abutting the cervix. A piston is actionable from inside the vagina to expel the contents of the container into the uterine cavity. This device is complicated by the incorporated embryo ejection means and does not admit readily of microscopic examination of the embryos prior to ejection. Moreover, it is not possible to simply and precisely locate embryos in the container for examination.

An object of the present invention is to provide a fertilization and culture container in which embryos may be easily located and/or inspected in situ and retrieved by direct transfer from the container, e.g. to the uterine cavity, by means of a catheter or pipette or the like.

Another object is to provide assisted procreation specialists with an improved novel method for conducting fertilization and culture and embryo inspection and transfer with a suitable container therefor so that the method may be readily carried out in the physician's office without the aid of sophisticated laboratory equipment or the heretofore requisite manual dexterity and experience of a laboratory biologist.

According to an aspect of the invention, there is provided a fertilization and culture container comprising a container body having an orifice and resealable closure means for selectively opening and closing the container body orifice. The container body has a main chamber for receiving the culture medium, oocytes and sperm and a microchamber for collecting for retrieval of one or more embryos. Preferably, the container body has means for restricting access of a retrieval catheter or the like relative to the microchamber.

Preferably, the microchamber has one or more parallel transparent sidewalls of optical quality for microscopically inspecting one or more embryos in the microchamber.

Preferably, there is an internal volume of the main chamber is between about 1 ml and about 5 ml and the microchamber has an internal volume of less than about 100 µl and preferably in the range of about 30 µl to 70 µl and is adapted to collect one or more embryos for microscopic inspection and/or retrieval.

Preferably, the capsule for enveloping the container, the capsule being made of soft elastic material having a smooth and continuous outer surface, and deformable cushioning means disposed proximate to an end of the capsule for adapting the longitudinal dimensions of the assembly to a chordal dimension of the posterior fornix when the intravaginal fertilization and culture container is received therein.

Preferably, a two-part tubular capsule is provided for enveloping the container, one of the parts having an inwardly extending central plug adapted to be received in and to seal off the passageway in the closure.

According to another aspect of the invention, there is provided an improved method including the steps of incubating gametes in a closed IVC container, allowing migration of the resulting embryo or embryos to the microchamber, retrieving the embryo or embryos directly from the microchamber with a catheter or pipette for transfer.

These and other objects and advantages of the present invention will be brought out in the description of embodiments given by way of example with reference to the accompanying drawings, wherein:

Figure 1:
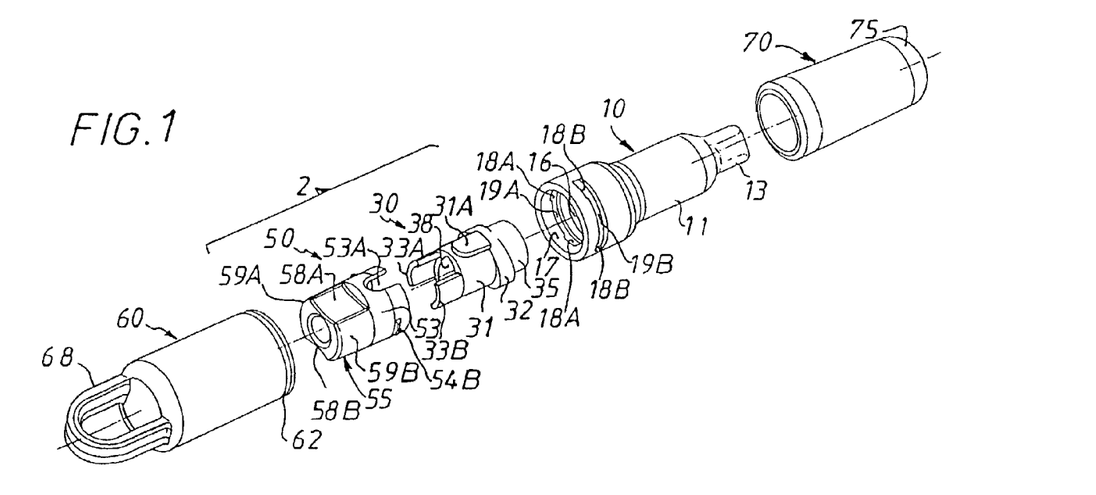
FIG. 1 is an exploded general view, in perspective, of the intravaginal fertilization and culture or IVC container assembly embodying various aspects of the invention.
Figure 3A:
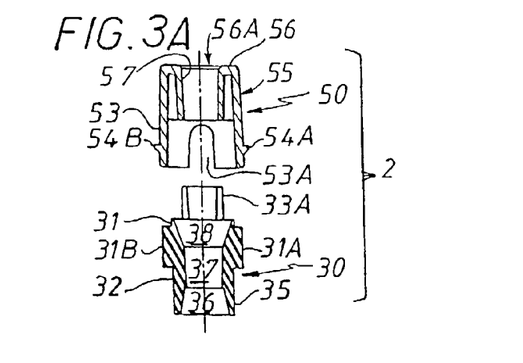
FIG. 3A is a longitudinal sectional view of the container cap and valve member of the present IVC container axially aligned but spaced from each other.
Figure 3B:
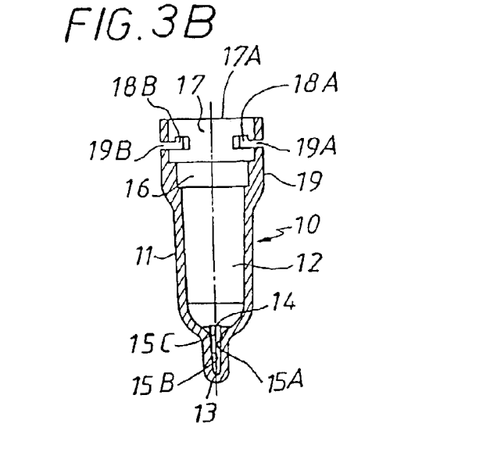
FIG. 3B is a longitudinal sectional view of the present IVC container body taken on its own.

According to a preferred embodiment of the invention, the IVC container 1 comprises a container body 10, resealable closure means 2 including a valve member 30 and a valve actuator member 50. The parts of the container are best shown in FIGS. 1, 3A and 3B and the assembled container in FIG. 4 inter alia. The container body and actuator member are preferably molded from polyethylene, polypropylene or other biocompatible relatively rigid biocompatible plastics materials. This plastics material should be $CO_2$ permeable in order to enable that gas to permeate the container wall from the vagina into the contained culture medium. (See Misao Fukuda et al, Unexpected low oxygen tension of intravaginal culture, Human Reproduction, vol. No 6, pp. 1285-1295, 1996.)

The container body has a generally cylindrical sidewall 11 defining a main chamber 12, and a microchamber 13 in communication with the main chamber. As illustrated and preferred, the microchamber is disposed at the closed forward end of the container body beyond the forward end of the main chamber and remote from the open rear end 17A of the container body 10. (Terms "forward" and "rear", and the like are used in the description and claims for the sake of convenience of the description only, and in and of themselves are not determinative of container orientation at any particular moment of the present procedure.) Alternatively, but not illustrated, the microchamber may be disposed along a generatrix or longitudinal line of the main chamber so as to project laterally from the sidewall. For reasons of facilitated embryo retrieval with a catheter and bulk, inter alia, the illustrated arrangement of the microchamber will generally be preferred.

Figure 9:
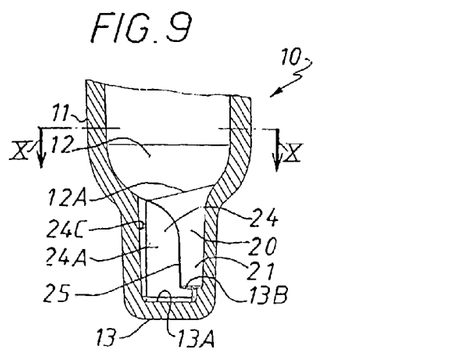
FIG. 9 is an enlarged detail longitudinal sectional view of the forward end of the container body with the microchamber.
Figure 10:
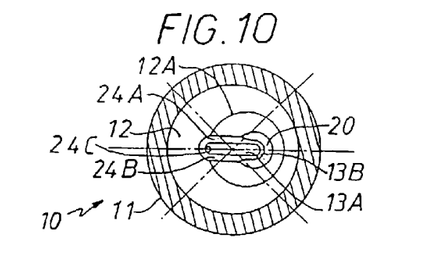
FIG. 10 is a cross sectional view taken along line X-X in FIG. 9.

The microchamber 13, best understood with reference to FIGS. 9 and 10, comprises opposed flat parallel sidewalls 24A, 24B, at least one of which and preferably both of which are of optical quality to permit microscopic inspection of embryos therethrough. The distance between the inner surfaces of the parallel sidewalls 24A, 24B of the microchamber is selected to be greater than embryo diameter so as to avoid embryos getting stuck in the microchamber but preferably close enough to retard displacement of the embryo in the culture medium. A distance between the microchamber sidewalls is less than about 1 mm and preferably about 0.5 mm or less for human as well as cow embryos. The sidewalls of the microchamber are joined by a longitudinally extending part cylindrical transverse wall 24C to one side of the microchamber. The microchamber 13 also includes a forwardly tapering radially offset funnel-shaped channel 20 extending from a port 12A of communication with the main chamber 12 towards the front endwall 13A of the microchamber. The rest of the microchamber defines a generally flat rectangular part 24 in communication with the channel 20 along a curved longitudinal port 25 therebetween. The curved longitudinal port 25 has a widely flaring upper funnel portion which extends practically to the transverse wall 24C of the microchamber opposite the channel. The forward end of the channel 20 farthest from the port 12A of communication, is spaced from the extreme end of the microchamber by a distance of at least 0.5 mm. This will leave space for at least five human embryos, average diameter of 0.1 mm at this stage of development and about four cow embryos, average diameter of 0.12 mm at the same stage of development.

Figure 13:
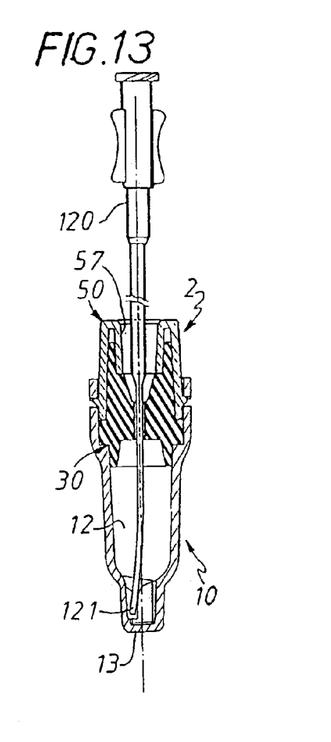
FIG. 13 is a longitudinal sectional view of the container with its valve member in the open position, and a catheter penetrating into a channel communicating with the microchamber for retrieval of embryos.

The forward end of the channel 20 is defined in part by a part circular (about 270°) ledge 13B in the transverse wall and sidewalls of the microchamber (see FIG. 10). The forward part of the channel 20 will preferably be configured to accommodate the tip of a retrieval catheter 120, as illustrated in FIG. 13 such as a Frydman or Wallace catheter widely used for transfer of embryos in IFC and IVC or some other embryo retrieval and transfer catheter or the like.

It goes without saying that the interior surface of the main chamber 12 and microchamber 13 are smooth and rounded throughout and devoid of any surface roughness or sharp edges liable to damage gametes or embryos.

In the rear section 19 of the main chamber 12 remote from the microchamber 13, is located a first cylindrical portion 16 of oval cross section adapted to cooperate with a corresponding oval flange portion 32 of the valve member 30 as described below. A second cylindrical section 17 of larger diameter than the major axis of the oval portion extends from the rear open end 17A to the first cylindrical section 16. Midway along the portion of the sidewall defining the cylindrical section 17 are a pair of diametrically opposed circumferentially extending part annular (approximately 90° arcs) guideways 18A and 18B having axially enlarged slot ends 19A, 19B. The guideways and slot ends are cooperable with detents 54A, 54B provided on the actuator member 50 and described below.

The valve member 30 is preferably made of a biocompatible deformable plastic or other synthetic material, and preferably silicone of high purity. The constituent material will be compliant so that the resealable access opening it defines may hemetically close off the main chamber of the container body. The valve member 30 comprises from its front end to its rear end, in axial succession, a tapered skirt 35, an oval flange 32 protruding radially outwardly beyond the tapered skirt and complementary in cross section to the oval cylindrical section 16 of the container body and adapted to mate therewith in the open position of the valve member. Rearward of the flange 32 is a cylindrical intermediate portion 31 having a pair of radially protruding, longitudinally extending bosses 31A, 31B, diametrically opposed to one another, and therebeyond at the rear end of the valve member, a pair of part cylindrical prongs 33A and 33B facing each other and extending over arcs of about 110°.

The interior of the valve member 30 comprises from its front end to its rear end a continuous passageway defining the access opening to the main chamber and including a forwardly diverging frustoconical section 36 of elliptical cross section connected to a slightly forwardly converging intermediate section 37 also of elliptical cross section, followed by a more markedly forwardly converging rear section 38, also of elliptical cross section. It will be noted that the major axes of the elliptical cross sections of the passageway through the valve member are substantially orthogonal to the major axis of the oval or elliptical flange 32 thereon.

The valve operating member 50 is preferably made of relatively rigid polyethylene such as high density polyethylene, low density polyethylene or a high density copolymer thereof, or a polypropylene homopolymer. The operating member 50 forms a cap for the container body and comprises a sidewall extending from a forward end to a rear end and includes a forward section 53 and a rear section 55. The forward and rear sections are substantially cylindrical with a slight forward flare and have generally circular cross sections. The forward section 53 comprises diametrically opposed cutouts 53A and 53B extending longitudinally from the forward edge rearwardly. Each diametrically opposed cutout 53A, 53B has a straight section with parallel longitudinal sides and a round rear end. The configuration of the cutouts is complementary to the outer contour of bosses 31A and 31B so as to snugly receive the same.

Diametrically opposed circumferentially extending detents 54A, 54B are disposed midway along the forward section 53 of the operating member 50 and regularly spaced from the cutouts 53A, 53B at approximately 90° from their respective mid-points. The detents 54A, 54B are adapted to be respectively received in the guideways 18A, 18B in the rear section 19 of the container body 10.

The rear section 55 of the operating member 50 comprises a pair of diametrically opposed concave wall portions 58A, 58B, for the operator's fingers, which alternate with convex wall portions 59A, 59B which are in smooth continuity with the forward section 53 of the operating member. The operating member has a part annular rear endwall 56 which extends between the rear edges of the concave 58A, 58B and convex wall portions 59A, 59B and a central aperture 56A. The inner periphery of the rear endwall 56 is joined to a forwardly tapering interior sleeve 57 radially spaced from the sidewall of the rear section 55 of the operating member 50 for receiving therebetween the complementarily shaped prongs 33A, 33B on the valve member 30.

Preferably, for assembly purposes, the valve member 30 is initially inserted into the operating member 50 with the prongs 33A, 33B received in the rear section of the cap between the interior sleeve 57 and the sidewall of the rear section 55 of the operating member and the bosses 31A, 31B received in the cutouts 53A, 53B. Once sub-assembly 2 of the operating member 50 and valve member 30 is formed, the forward section 53 of the cap, is pushed axially inside the rear cylindrical section 17 of the container body until the detents 54A, 54B snap into guideways 18A, 18B. Thus assembled, the operating member 50 can be rotated clockwise or counter clockwise to stable rest positions where the detents are received in the enlarged portions 19A and 19B of the guideways and where short longitudinal shoulders oppose inadvertent rotation of the operating member from the stable end positions. The stable rest positions correspond, respectively, to the open and closed position of the valve member.

Figure 6:
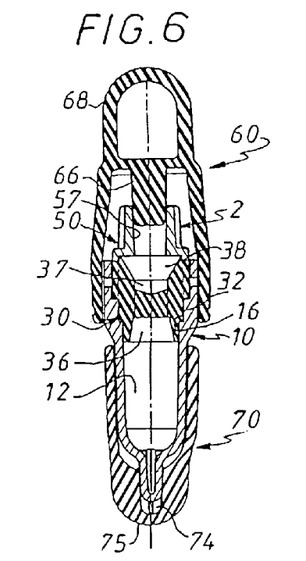
FIG. 6 is a longitudinal sectional view of the IVC container assembly, taken at 90° from that of FIG. 4A, with the valve member in its closed end, the capsule being partway received on the container.
Figure 8A:
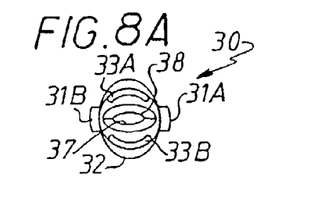
FIG. 8A is rear end view of the valve member, in its open position.
Figure 8B:
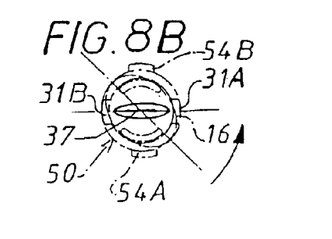
FIG. 8B is a view similar to FIG. 8A showing the valve member in its closed position.

As the operating member 50 is rotated 90° from an open position to a closed position, the oval flange 32 is deformed owing to the non-complementary orientation of the oval cylindrical portion 16 of the container body thereby deforming the intermediate portion of the valve member 30 as shown in FIG. 6 to bring walls of the elliptical intermediate section 37 from the position shown in FIG. 8A in flattened mating contact as illustrated in FIG. 8B and thereby collapsing the passageway of the valve member 35 and the sealing off the access opening to the main chamber and closing off communication between the main chamber 12 of the container body and the surroundings.

Figures 4A, 4B:
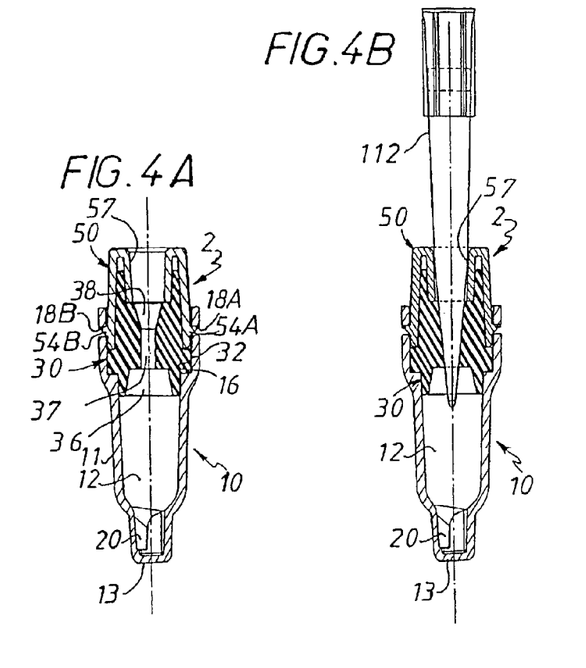
FIG. 4A is a longitudinal sectional view of the present IVC container, with the valve member in its open position.
FIG. 4B is a longitudinal sectional view of the present IVC container and a pipette for introducing culture medium, oocytes and/or sperm into the main chamber.

The operation of the present IVC container will now be described. First, the container is assembled and the valve member 32 is opened as illustrated in FIG. 4A. At this point, the culture medium is introduced into the main chamber and microchamber by means of a standard pipette such as illustrated in FIG. 4B and identified by reference numeral 112. The frustoconical internal sleeve 57 will cooperate with the tapered wall of the pipette so that in the fully inserted position, the outlet orifice of the pipette is well into the main chamber and, as illustrated, below the forward end of the skirt 35 of the valve member. The main chamber and microchamber will be filled to the level of the frustoconical section 36, and in practice just below the rearmost part thereof. The culture medium of choice is INRA Menoza B2 Medium available from Laboratoire C.C.D. in Paris. Thereafter, the oocytes and sperm are introduced by means of a catheter or pipette. Generally, 60,000 to 300,00 motile sperm and more particularly 100,000 motile sperm and 1 to 5 oocytes will preferably be used. However, in certain cases, involving a severe male factor, more than 300,000 up to 500,000 motile sperm may be used.

The sperm may be introduced either before or after the oocytes or even at the same time. Generally, it will be preferred to introduce the sperm before or at the same time as the oocytes.

At each stage of the filling procedure, the valve member can be closed. Thus, when employing a catheter, the valve member can be substantially closed around the catheter without obstructing the flow of oocytes and/or sperm. Closure of the valve member will of course ensure minimal contact between the surrounding air and the chambers of the container.

Prior to intravaginal incubation, the closed IVC container is preferably heated for about one hour in an incubator operating at 37° C. The container will preferably not be enveloped in the capsule used during incubation.

Figure 5A:
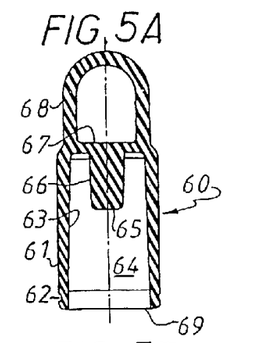
FIG. 5A is a longitudinal sectional view of a rear part of the capsule.
Figure 5B:
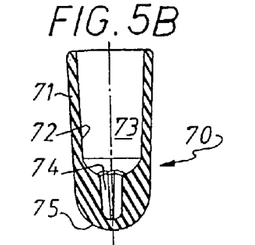
FIG. 5B is a longitudinal sectional view of a forward part of the capsule.

In order to prevent contamination of the contents of the container during intravaginal residence and to avoid any injury in the course of introducing, removing and residence of the container 1, it is enveloped after preliminary heating in the incubator in a capsule of soft smooth biocompatible material such as silicone. Preferably, the capsule comprises forward and rear capsule portions 70 and 60, illustrated in FIGS. 5A and 5B adapted to be received over the respective ends of the container 1, as illustrated in FIG. 6. If desired, these separate capsule portions may be joined together for example by a preferably stretchable longitudinal strap or the like, not shown.

The forward capsule portion 70 comprises a generally cylindrical sidewall 71 with a slight rearward flare and a rounded end wall 75. The forward capsule portion 70 has an inner wall defining a main compartment 73 adapted to mate with the portion of outer sidewall 11 defining the main chamber and a generally flat rectangular microcompartment 74 having a round forwardmost wall, the microcompartment formed into the closed thickened end of the capsule portion 70 being complementary to the configuration of the outer walls of the microchamber 11. The forward capsule portion 70 can be slid or unrolled on to the container body 11 from the microchamber end rearwardly towards the open end of the container body. When the forward capsule portion 70 is fully received on the container body, the free edge of the capsule sidewall 71 will slightly overlie the forward part of a forwardly tapering frustoconical portion interconnecting the cylindrical sidewall 11 and the rear section 19 of the container body (see FIG. 7).

Figure 7:
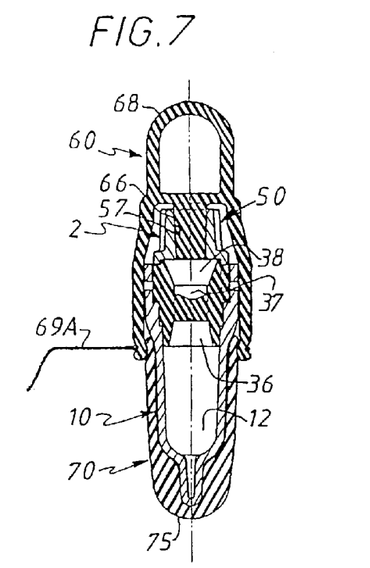
FIG. 7 is a longitudinal sectional view of the entire IVC container assembly, with the valve member in its closed position and the capsule entirely enveloping the container.

The rear capsule portion 60 also comprises a generally cylindrical sidewall 61 extending between an open forward end 69 and a closed rear end 67. The rear capsule portion 60 has an inner wall 63 defining a forwardly flaring compartment 64 generally complementary to the operating member 50. The endwall 67 has a forwardly tapered plug 66 adapted to matingly engage the tapered interior sleeve 57 of circular cross section of the operating member. The inner surface of the endwall 67 may remain spaced from the endwall 56 of the operating member in the fully inserted position, as illustrated. Second sealing tier is defined between the plug and the interior sleeve of the cap. Sidewall 61 of the rear capsule portion 60 is adapted to extend over the rear section 19 of the container body and beyond the adjoining frustoconical connecting zone of the sidewall and over the free edge portion of the forward capsule 70, thereby entirely enveloping the container, as illustrated in FIG. 7.

Attached to and integral with the rearwall 67 of the rear capsule portion 60 is a rearwardly extending U-shaped loop 68 having opposed longitudinal legs and a round bight or intermediate portion connecting the legs remote from the rearwall 67. The main function of loop 68 is to define an axially deformable cushioning means adapting the effective length of the IVC assembly to the chordal length of the individual's posterior fornix. When the posterior fornix is of small dimensions as is often the case prior to first child birth, the deformable loop will be flattened against the endwall 67 so that it protrudes transversely to the axis of the assembly. The loop is of sufficiently soft and pliable material that the resulting compression will cause no discomfort. With a posterior fornix of larger dimensions, the deformable loop 68 will be only slightly deformed to a more or less bow-legged U-shape, the loop thus ensuring that the IVC assembly is snugly held so that the undesired displacement or release of the IVC container in the posterior fornix is substantially eliminated. The length of the assembly for the human anatomy with the loop in its erect position will be about 7.5 to 9 cm and with the loop flattened against rearwall 67 about 6 to 6.5 cm. For use in cows or other large mammals, the overall length of the assembly in the erect position of the loop will be between 10 and 15 cm and preferably about 12 cm. It may be possible to obtain the extended length by simply partially withdrawing rear and forward capsule portions to the position illustrated in FIG. 6 whereby a single size IVC container assembly may have both human and other mammalian applications. It is noted that in the FIG. 6 position, the intermediate portion of the container body sidewall will be exposed. To avoid such exposition, a wide elastic band may be brought in position over the free edge portions of the forward and rear capsule portions.

The IVC assembly may be disposed in the posterior fornix so that the loop 68 is oriented anteriorly. In this case, the loop 68 may provide a convenient appendix for attaching a fine plastic tie or string to the IVC container assembly. Alternatively, and as illustrated, a fine plastic tie or string is received in an annular groove 62 in the sidewall 61 of the rear capsule portion, adjacent the open forward end thereof. The plastic tie 69A is tightened around the groove 62 thereby compressing and deforming the free edge of the rear section against the free edge portion of the forward section and thus improving the sealing of the capsule. The dangling string 69A at this location is used to facilitate the removal of the IVC container assembly from the posterior fornix. (It should be noted that with the Nunc tube, the removal was done by the physician who needed a speculum for that purpose.)

The normal period of vaginal residence of the IVC assembly is between 48 and 72 hours. The assembly may be removed by the user or the physician from the posterior fornix by tugging on a string tie 69A and then removing the assembly from the vagina. Thereafter, the capsule portions 60 and 70 are slid or rolled off the container 1.

The embryo or embryos which have developed may then be inspected. To this end, the container will be first oriented as illustrated in FIG. 4A, but with the valve member closed. This will enable embryos emerged in the culture medium to fall or settle to the microchamber under the force of gravity. Then the container will be oriented so that the longitudinal axis is substantially horizontal and the flat part 24 of the microchamber is below the channel 22 so that all embryos will then be collected in that part. Thereafter, the container will be turned 90° so that the walls 24A and 24B of the microchamber are horizontal and then they are brought into alignment (at 90°) with the optical axis of the lab microscope (not shown).

Once the embryos have been inspected and the decision made as to which one or ones are to be implanted, a catheter 120 will be introduced into the container with its tip received into the channel, the selected embryo or embryos can then be aspirated into the catheter and then transferred to the uterine cavity for implantation in accordance with standard procedures. Preferably, the retrieval will be carried out under a microscope so that the orifice of the catheter may be positioned immediately adjacent the ooctye(s) to be retrieved, e.g. by tilting the container. During embryo retrieval, the valve member may be closed around the catheter to limit the communication of air with the contents of the container. Given the softness of the valve member material, here silicone, the access opening can be substantially sealed without interfering with embryo retrieval.

Figure 14:
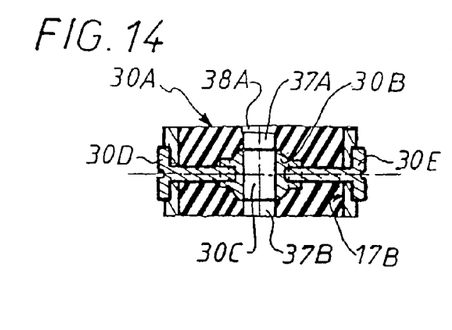
FIG. 14 is a partial longitudinal section of the valve device of the IVC container according to an alternative embodiment, in the open position of the valve

FIG. 14 illustrates the container with the valve member in its open position so as to define an orifice for accessing the interior of the container body 10. A Frydman or Wallace catheter 120 is inserted through the access orifice and the end or tip 121 thereof is received in channel 20. Penetration of the end of the catheter into the channel is limited by the shoulder 13B at its forwardmost end against which the tip of the catheter abuts upon full penetration. The distance between the shoulder and the forward endwall of the microchamber is sufficient (about 0.5 mm) to accommodate about five human embryos, one on top of another, without any risk of injury by the tip of the catheter. The forwardly tapering junction zone or port 25: between the channel and the flat rectangular part 24 of the microchamber 13 ensures the tip of the catheter will be guided into the channel and to the forwardmost end thereof without posing any difficulty for the physician.

The container will be oriented with its axis generally horizontally and the channel above the flat rectangular part 24 of the microchamber 13 immediately prior to catheter introduction so that embryos which may have been collected in the channel may migrate to the flat part 24 of the microchamber whereby under the force of gravity to avoid the embryos being pinched between the catheter and the ledge 13B.

The container may then be disposed in its upright or recumbent position. Once the catheter tip 121 is in position relative to the microchamber, the catheter can aspirate the embryos from the flat part 24 of the microchamber through the retrieval aperture of the catheter. The loaded catheter can then immediately be used to transfer the embryo or embryos to the uterus for implantation.

Figure 11:
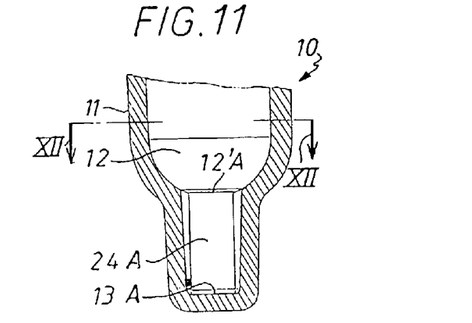
FIG. 11 is a view to that of FIG. 9 for an alternative embodiment of the microchamber.
Figure 12:
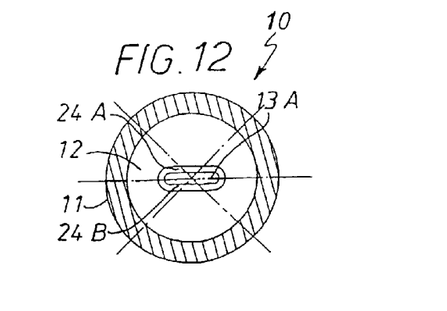
FIG. 12 is a view similar to that of FIG. 10 taken along line XII-XII in FIG. 11.

Similarly in the FIGS. 11-12 modified embodiment the narrow access port 12'A defined by pairs of parallel edges and concave edges between the main chamber 12 and the microchamber 24 will prevent any significant penetration of the tip of the catheter into the microchamber as the tip has a diameter greater than the narrow transverse dimension of the access port. For this embodiment, the tip of the catheter will be free to move back and forth along the access port during embryo retrieval. Alternatively, the catheter tip can be applied against a concave ledge of the narrow access port to locate the same in a relatively stable position during this step.

In lieu of a catheter, a pipette of standard configuration may be employed to retrieve embryos from the microchamber. The pipette may have a tapered tip adapted to be received in the channel of the FIGS. 1-10 embodiments.

Accordingly, at no time, from the moment gametes are introduced into the culture medium in the container body until the moment embryos are retrieved for transfer to the uterus are the gametes or embryos directly in contact with air and the surroundings. Thanks to the disclosed invention, it will be possible to inspect embryos microscopically without removing them from the IVC container avoiding contact with the surroundings and also to view them during positioning relative to the catheter or pipette orifice, in particular by tilting the container. It will also be appreciated that throughout the entire fertilization and culture procedure, the contents of the IVC container will be protected from contamination by resealable closure means defined by the valve member, and second tier sealing defined by the plug on the rearward capsule portion matingly received into the tapered interior sleeve of the cap. Another level of protection is defined by the capsule itself which entirely envelopes the closed and sealed container and defines an aseptic barrier to prevent tunneling of bacteria and viruses present at the vaginal cavity and thereby reduce the risk of contamination of embryos when opening and removing the same for transfer. It will also be understood that owing to the narrow elliptical access orifice through the valve member in the open position or partly open, when gametes are introduced or embryos removed, contact with environing air will be practically eliminated.

In the closed position of the valve member, the forwardly flaring front section 36 of the passageway and the adjoining annular edge of the skirt 35 define the rear end of the main chamber. It would be understood that this configuration will impede the oocytes from flowing back into the intermediate section of the valve member passageway where they could otherwise be inadvertently held captive inside the mating walls of the valve member passageway or even crushed and in any event held out of contact with the culture medium and sperm. Moreover, when the valve member is open or partly open, the catheter will partly fill the access opening.

Figure 15:
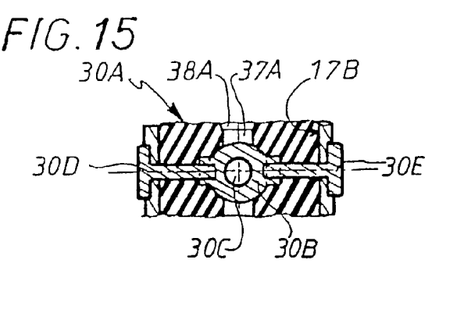
FIG. 15 is a view corresponding to FIG. 14 in the closed position of the valve.

Other resealable closure means and more particularly valve designs may be employed with the present IVC container. According to a preferred embodiment of the resealable closure device illustrated in FIGS. 14 and 15, a silicone plug 30A with an axial aperture and a central valve member cavity is fitted into a rear end section 17A of the container body similar to that of the second section 17 without any circumferential slot and without the first cylindrical section 16. The silicone plug 30A of cylindrical configuration and circular cross section will have forward and rear passageway sections 37A, B extending generally axially for accessing the main chamber and/or microchamber when the valve member 30A is in its open position (see FIG. 14). The valve member is journaled in the sidewalls of the rear end section 17A of the container body for rotational movement about a transverse axis orthogonal to the axis of the container body, between an open position (FIG. 14) in which a passageway 30B through the valve member 30A is in alignment with the passageway sections 37A, 37B through the plug and a closed position (FIG. 15) when the valve member 30A obstructs communication between the aligned passageway sections in the plug, the passageway section in the valve member being at right angles to those in the plug. At the end of the journals in the sidewalls of the container body, disclike operating members 30A, 30D (which may be slotted for a screwdriver) will be accessible to the physician's fingers to apply pressure to the operating members and turn the valve member, overcoming the friction between, inter alia, the valve member and the mating cavity in the plug accommodating the valve member. In such an embodiment, the relatively rigid valve member which is relatively rigid is accommodated in a relatively soft silicone plug 30A is used to open and close access to the container chambers, as opposed to the illustrated embodiment which employs an elastically deformable valve member to close the passageway by rotating a relatively rigid operating member about the axis of the container.

Alternatively, the valve member and cavity in the plug may be of ovoid shape (not illustrated), with the major axis orthogonal to the container axis. For either of these embodiments, the cooperable stop means (not shown) on the container rear end section and the resealable rigid valve member will define the range of angular displacement of the valve member, limited to approximately 90°.

It would be appreciated that these and other modifications and variants of the container and the container assembly may be adopted without departing from the spirit and scope of the invention defined by the appended claims.

The invention claimed is:

1. An intravaginal culture (IVC) container comprising a container body for the culture of one or more embryos in a culture medium, the container body being sized and configured for intravaginal accommodation, a resealable closure for the container body, the resealable closure permitting selective access to the interior of the container body, the container body interior including a main chamber and a microchamber in communication with the main chamber, the microchamber being configured for collecting and retrieval of the one or more embryos.

2. The IVC container according to claim 1, wherein the container body has a portion for restricting access of a retrieval catheter or pipette relative to said microchamber.

3. The IVC container according to claim 2, wherein the container body portion for restricting access of a retrieval catheter or pipette is defined by an inlet port of the microchamber through the main chamber for restricting penetration of the retrieval catheter or pipette into the microchamber.

4. The IVC container according to claim 2, wherein the container body portion comprising a channel extending from the main chamber into the microchamber and complementary in configuration to an end portion of a retrieval catheter or pipette to position a catheter or pipette tip spaced from a forward endwall of the microchamber when the retrieval catheter or pipette is fully penetrated into the container body.

5. The IVC container according to claim 1, wherein at least a portion of a sidewall of the container body defining said microchamber is transparent and of optical quality for microscopic inspection of the one or more embryos.

6. The IVC container according to claim 4, wherein the microchamber has opposed parallel transparent sidewalls of optical quality extending laterally from said channel.

7. The IVC container according to claim 1, wherein the volume of the microchamber is less than about 100 μl.

8. The IVC container according to claim 1, wherein the volume of the microchamber is between about 25 μl and about 70 μl.

9. The IVC container according to claim 6, wherein the width of the microchamber measured between the opposed parallel sidewalls is between about 0.3 and about 0.8 mm.

10. The IVC container according to claim 9, wherein the average diameter of the forward portion of the catheter channel is between about 2 mm and about 3 mm.

11. The IVC container according to claim 1, wherein the resealable closure comprises an orifice of the container has a portion for positioning a catheter or pipette end relative to the main chamber forwardly of the resealable closure.

12. The IVC container according to claim 1, further comprising a soft, pliable capsule for enclosing the container including at least two parts adapted to be slipped over the container from opposite ends thereof, said capsule parts having free edge portions overlappable for sealing the capsule, the IVC container and the capsule together defining an IVC container assembly.

13. The IVC container assembly according to claim 12, wherein said capsule defines a deformable cushion disposed proximate an end of said capsule for adapting the longitudinal dimensions of the IVC container assembly to a chordal dimension of the posterior fornix when the IVC container assembly is received therein.

14. The IVC container assembly according to claim 1, wherein further comprising a soft, pliable capsule for enclosing the container, the IVC container and the capsule together defining an IVC container assembly, said soft elastic material defining an aseptic barrier to prevent tunneling of bacteria and viruses present in the vaginal cavity and reducing the risk of contamination of embryos.

15. The IVC container according to claim 1, wherein a free access zone for communication between the main chamber and the microchamber and passage of the culture medium and the one or more embryos immersed in the culture medium therebetween.

16. The IVC container, according to claim 1, further comprising, in combination therewith, a retrieval catheter or pipette from the microchamber for retrieval of the one or more embryos in said culture medium, said microchamber having one or more transparent zones for viewing the one or more embryos therein, prior to and/or during retrieval.

17. A method of intravaginal culture (IVC) comprising the steps of:
providing an IVC container sized and configured for intravaginal accommodation, the IVC container including a container body and a resealable access opening to the interior of the container body, the interior of the container body including a main chamber and a microchamber in communication with each other and containing a culture medium;
vaginally incubating at least one embryo in the IVC container;
allowing migration of the at least one embryo into the microchamber;
removing the IVC container from the vagina; and
retrieving the at least one embryo from the microchamber for transfer.

18. The method of intravaginal culture (IVC) according to claim 17, further comprising vaginally incubating for about 48 to about 72 hours.

19. The method of intravaginal culture (IVC) according to claim 17, further comprising the step of microscopically inspecting the at least one embryo in the microchamber prior to and/or during retrieval.

20. The method of intravaginal culture (IVC) according to claim 17, wherein migration of the at least one embryo is assisted by orienting the container so that the microchamber is disposed below the main chamber.

21. The method of intravaginal culture (IVC) according to claim 17, further comprising the step of enveloping the container in a soft flexible capsule prior to vaginal incubation.

22. The method of intravaginal culture (IVC) according to claim 21, wherein said capsule has a deformable cushion for adapting its dimensions to the posterior fornix.

23. The method of intravaginal culture (IVC) according to claim 21, further comprising the step of attaching a string to the capsule for facilitating retrieval of the container from the posterior fornix.

24. The method of intravaginal culture (IVC) according to claim 17, further comprising the step of restricting access of a catheter or pipette into the microchamber and orienting the container so that the main chamber is disposed above the microchamber before embryo retrieval with the catheter or pipette.

25. The method of intravaginal culture (IVC) according to claim 17, further comprising the step of limiting the penetration of the free end of the catheter or pipette into microchamber, so as to accommodate at least five embryos between the free end of the catheter or pipette and the forward endwall of the microchamber.

26. The method of intravaginal culture (IVC) according to claim 17, further comprising the step of providing the container with an access passageway upstream of a resealable closure for sealingly plugging the access passageway by encapsulation of the container.

* * * * *